United States Patent [19]
Cottone et al.

[11] Patent Number: 5,707,173
[45] Date of Patent: Jan. 13, 1998

[54] FLUID COLLECTION DEVICE

[75] Inventors: Anthony J. Cottone, Ball Ground; Joseph R. Cottone, Sr., Marietta, both of Ga.

[73] Assignee: Advanced Medical Designs Inc., Marietta, Ga.

[21] Appl. No.: 496,331

[22] Filed: Jun. 29, 1995

[51] Int. Cl.$^6$ .................................................. B09B 3/00
[52] U.S. Cl. .................. 405/128; 206/366; 588/249; 588/259
[58] Field of Search ...................... 588/249, 258, 588/259, 260, 261; 206/366

[56] References Cited

U.S. PATENT DOCUMENTS

| | | | |
|---|---|---|---|
| 4,328,904 | 5/1982 | Iverson | 206/315 R |
| 5,236,088 | 8/1993 | Dhority et al. | 588/258 X |
| 5,245,117 | 9/1993 | Withers et al. | 588/249 |
| 5,323,719 | 6/1994 | Withers et al. | 206/366 X |
| 5,328,028 | 7/1994 | Hale et al. | 588/258 X |
| 5,372,252 | 12/1994 | Alexander | 206/366 X |
| 5,385,105 | 1/1995 | Withers et al. | 206/366 X |
| 5,411,193 | 5/1995 | Culp | 206/366 X |
| 5,483,999 | 1/1996 | Lampropoulos et al. | 206/366 X |

FOREIGN PATENT DOCUMENTS

| | | | |
|---|---|---|---|
| 2251423 | 7/1992 | United Kingdom | 206/366 |

OTHER PUBLICATIONS

Photographs and label for the "Backstop Disposal System" sold by Merit Medical Systems, Inc. of Salt Lake City, Utah 84107.

*Primary Examiner*—Dennis L. Taylor
*Attorney, Agent, or Firm*—Jones & Askew

[57] ABSTRACT

A disposable back table collection device having a container with an open end and at least one layer of an absorbent material positioned within the container. The open end of the container is sealed with a cover containing a leak resistant injection site. The invention also may have a second layer of an absorbent material positioned on top of the cover with an aperture therein corresponding to the location of the injection site. In use, a syringe is inserted into the injection port and the syringe is drained. The fluid from the syringe is absorbed into the layer of absorbent material. When the syringe is removed, the injection port has sufficient elastic "memory," or shape retaining characteristics, to return to its original position, thereby insuring a leak resistant seal. Further, there is no splashing while the syringe is either inserted or removed because any droplets of fluid that may escape from the syringe are absorbed into the absorbent material on the top of the device. The result is a leak resistant, splash resistant disposable back table collection device.

11 Claims, 2 Drawing Sheets

FLUID COLLECTION DEVICE

TECHNICAL FIELD

This invention relates generally to fluid collection devices and, more particularly, to a disposable, spill resistant, splash resistant collection device for waste or contaminated fluids present during medical procedures.

BACKGROUND OF THE INVENTION

Numerous medical procedures involve the use of various types of syringes for the transfer of blood, dyes, and other fluids into and out of the body or through intravenous lines. For example, angiography, angiocardiography, and similar procedures involve the injection of radiopaque fluids or other substances into the body for subsequent evaluation by X-ray and other imaging techniques.

Fluids are transferred directly to or from the body via needle-type syringes and into intravenous lines via blunt-tip syringes. These needle-type syringes must be drained before they can be properly disposed of. Syringes used with intravenous lines can be used several times during the same procedure. These syringes, however, also must be drained after each use and at the end of the procedure.

While syringes and similar devices must be quickly drained during medical procedures in a convenient manner for the user, the means of disposal must minimize the risk that the user may be splashed or sprayed with the fluid. The danger of this type of spilling, sloshing, and splashing has been recognized by federal health regulations. Current government regulations require that contaminated material such as blood, dye, and other fluids used in medical procedures, clinical laboratories, research laboratories, production facilities, and elsewhere, be disposed of in a manner that prevents or limits human contact. These regulations, promulgated by the Occupational Safety and Health Administration ("OSHA"), require "universal precautions" in the handling of any bodily fluid.

For example, regulations concerning blood borne pathogens require that fluids such as blood must be handled by medical workers in a manner to minimize the potential for spraying or splashing:

All procedures involving blood or other potentially infectious materials shall be performed in such a manner as to minimize splashing, spraying, splattering, and generating droplets of these substances.

29 C.F.R. 1910.1030(d)(xi).

Similar rules apply to the disposal of contaminated wastes and fluids:

Specimens of blood or other potentially infectious materials shall be placed in a container which prevents leakage during collection, handling, processing, storage, transport, or shipping.

29 C.F.R. 1910.1030(d)(xiii).

Known containers into which syringes are drained have been called "back table collection devices," because they often are placed on the back table of an operating theater or research laboratory. These devices are designed to hold the excess fluids that may remain in a syringe or other medical device. Known designs include, for example, a reusable open basin or waste bag of either metal or other leak proof material. The syringe is either placed over the basin or waste bag and drained or inserted into a matable tip or opening positioned over the basin or waste bag, drained, and removed. After the procedure is completed, the basin or waste bag is removed from the operating room or laboratory for the disposal of the fluid. The basin or bag is then sterilized for further use.

Another known approach to fluid disposal is the "Back-stop"™ device made by Merit Medical Systems, Inc. of Salt Lake City, Utah. This disposable device comprises a plastic container covered with a slightly concave or inverted plastic top. The top contains a large circular aperture at the bottom of the inversion that is covered with a circular piece of a foam material approximately two inches in diameter. The center of the foam is star cut. The interior of the container contains a "pillow" filled with a crystalline material that turns into a gel-like substance upon contact with a liquid. A syringe is inserted through the aperture and drained into the pillow.

While federal regulations require "universal precautions" in the handling of fluids, both the reusable and the disposable back table designs have several drawbacks. First, neither design is particularly spill or slosh resistant. Obviously, the open basin or waste bag may spill while being removed from the operating room or laboratory or if the basin is tipped. Further, while the disposable design has a top cover and contains a pillow of material that is intended to absorb the fluids, any fluid that has not been captured by the pillow can escape through the wide aperture, which is not sealed by the foam covering.

Second, a drawback with both designs is the potential for fluids either to seep out or accidentally be forced out of the syringe and splash the user while the syringe is being inserted or removed from the back table device. For example, because only the large central aperture is covered with foam in the disposable device, contaminated fluids may splash or spray off of the hard plastic cover and contact the user. Likewise, liquids can easily splash or spray off of the hard surface of the reusable basin or even off of the surface of the fluids already collected therein.

A further drawback with the disposable design is that the syringe tends to penetrate into the pillow and contact back the gel-like material. The gel may be forced under pressure back into the syringe and could be injected into the patient. Once this penetration of the pillow has occurred, the syringe is rendered useless and must be replaced.

In sum, the known back table collection devices simply do not provide the user with a system for the collection of fluid from a syringe that adequately protects the user from contact by either splashing or spraying. Further, these known devices tend to destroy the usefulness of the syringe. What is needed is a disposable back table collection device that is substantially spill resistant and splash resistant to ensure that contaminated fluids are properly and safely disposed of in accordance with government regulations. The device must accomplish these goals while being lightweight and easy to use. Further, the device must be relatively inexpensive to manufacture and distribute.

SUMMARY OF THE INVENTION

Generally described, the present invention provides a disposable back table collection device having a container with an open end and at least one layer of an absorbent material positioned within the container. The open end of the container is sealed with a cover containing a leak resistant injection site. The invention preferably has a second layer of an absorbent material positioned on top of the cover with an aperture therein corresponding to the location of the injection site.

Embodiments of the invention include the use of a layer of a large pore foam such as a reticulated ester filter foam as the layer of absorbent material. The second layer of absorbable material is preferably a polyurethane open cell foam. The cover preferably has a waterproof closing layer of high density polyethylene fibers, such as that sold under the trademark Tyvek™ spunbonded olefin material, and an elastic layer of thermoplastic rubber, such as that sold under the trademark Kraton™, heat sealed to the container. The leak resistant injection site incorporated in the cover is an aperture within the layer of elastic material.

The container itself is made from a lightweight plastic and has tapered sides to resist tipping. The bottom end of the container has a layer of adhesive tape positioned thereon. The container has sufficient clearance between the cover and the layer of absorbent material to permit the entry of a syringe tip into the leak resistant injection port without the syringe tip contacting the layer of absorbent material.

In use, a syringe is inserted into the injection port and the syringe is drained. The contaminated fluid is absorbed into the layer of absorbent material. When the syringe is removed, the injection port has sufficient elastic "memory," or shape retaining characteristics, to return to its original position, thereby insuring a leak resistant seal. Further, there is no splashing while the syringe is either inserted or removed because any droplets of fluid that may escape from the syringe are absorbed into the absorbent material on the top of the device. The result is a leak resistant, splash resistant disposable back table collection device.

It is thus an object of the present invention to provide an improved disposable back table collection device.

It is another object of the present invention to provide a spill resistant back table collection device.

It is a further object of the present invention to provide a splash resistant back table collection device.

It is a still further object of the present invention to provide a back table collection device that is easy to use.

It is a still further object of the present invention to provide a back table collection device that is stable and resists tipping.

It is a still further object of the present invention to provide a back table collection device that is inexpensive to manufacture.

Other objects, features, and advantages will become apparent upon reading the following detailed description of the preferred embodiment of the invention, when taken in conjunction with the drawings and the appended claims.

DETAILED DESCRIPTION OF THE INVENTION

Figure 1:
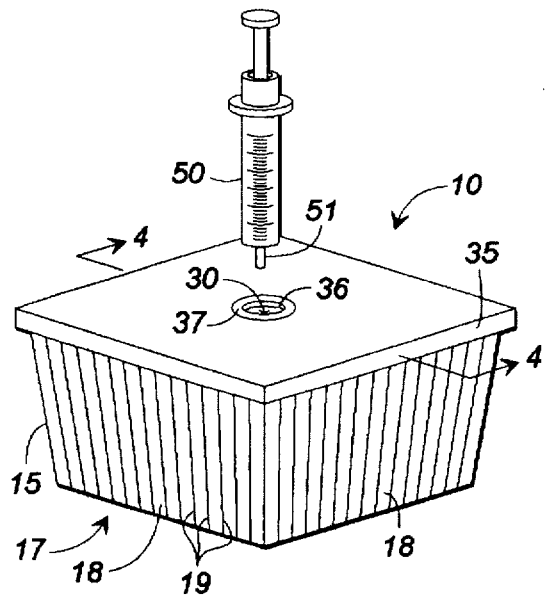
FIG. 1 is a perspective view showing the preferred embodiment of the fluid collection device with a syringe.
Figure 2:
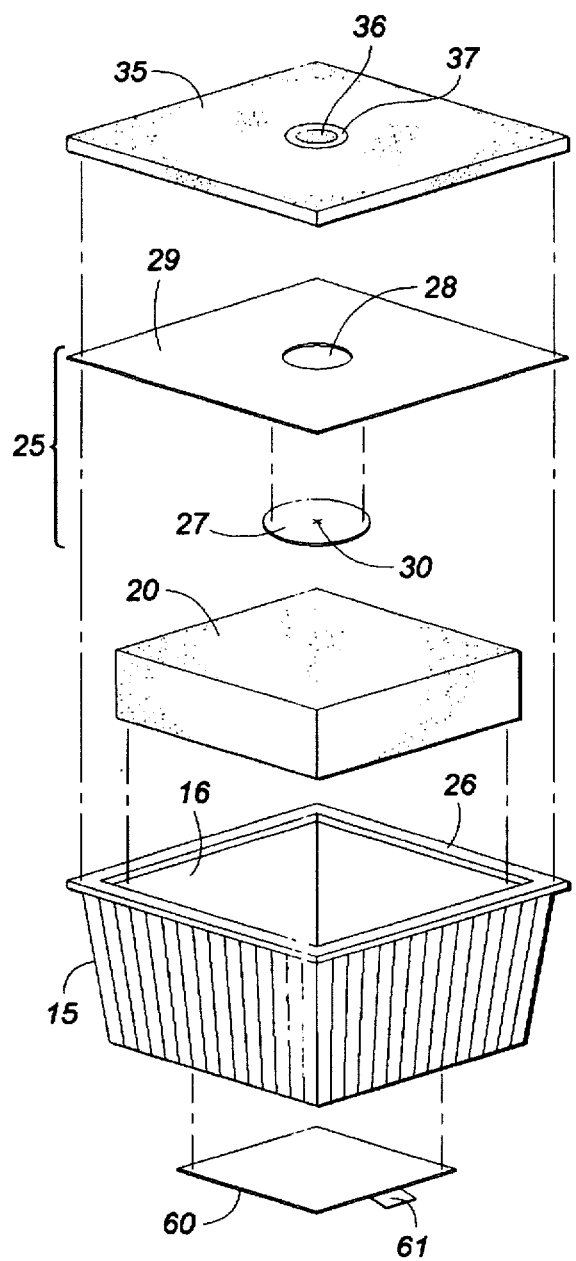
FIG. 2 is an exploded view showing the elements of the preferred embodiment of the fluid collection device.

Reference is now made to the figures, where like numerals designate like objects throughout the several views. As is shown in FIGS. 1 through 4, the major components of a back table collection device 10 according to the preferred embodiment of the subject invention include a container 15 with an open end 16, a layer of absorbent material 20 positioned within the container 15, a cover 25 positioned over and sealing the open end 16 of the container 15, a leak resistant injection site 30 centered on the cover 25, and a second layer of an absorbent material 35 positioned on the cover 25.

The container 15 is preferably manufactured from any type of substantially rigid and water proof material, such as light weight thermoformed plastic. The preferred embodiment of the invention employs a container 15 of thermoformed styrene. Heavy duty laminated cardboard or even lightweight metals also may be used. The container 15 preferably has a base 17 that is larger in area than the individual sides 18 to promote stability. The sides 18 also are preferably tapered slightly to increase stability and have molded-in ribs 19 for increased structural strength. In the preferred embodiment, the base 17 of the container 15 has a depth of approximately two and one-quarter inches and four tapered sides 18 with lengths of approximately four inches. The open end 16 of the container 15 is surrounded by a lip 26 for mating with the cover 25.

An adhesive substance 60, such as a two-sided strip of adhesive tape, is preferably added to the base 17 to insure stability while the device 10 is in use. One side of the adhesive substance 60 may be covered with a pull tab 61 until the device 10 is ready for use.

A layer of an absorbent material 20 is then positioned within the container 15. The layer of absorbent material 20 is preferably a large pore foam material, such a reticulated ester filter foam, or other material with significant absorption properties. The material used in the preferred embodiment is a coarse filter type foam with a cell count of approximately thirty pores per inch and a density of approximately 1.9 pounds per cubic foot. The layer of absorbent material 20 is preferably sized for a press fit within the container 15. The layer of absorbent material 20 is thick enough to absorb a significant amount of liquid but thin enough to avoid direct contact with a tip 51 of a syringe 50. The layer of absorbent material 20 of the preferred embodiment is approximately one inch thick, leaving about an inch of clearance for the tip 51 of an inserted syringe 50 between the cover 25 and the absorbent layer 20.

The cover 25 comprises a closing layer 29 to close and substantially seal the open end 16 of the container. The closing layer 29 is sized to fit and seal the open end 16 of the container 15 via a heat seal. The closing layer 29 can be any type of substantially water proof and water insoluble material, such as polyethylene fibers, laminated paper, cardboard, plastic, lightweight metals, or similar materials capable of bonding to the lip 26 of the container 15. In the preferred embodiment, the closing layer 29 comprises a layer of continuous, high density polyethylene fibers, such as that sold under the trademark Tyvek™ spunbonded olefin material by E.I. DuPont de Nemours & Co., Inc. of Wilmington, Del. The closing layer 29 has a thickness of approximately 10 mils or other conventional thickness for the material involved.

Figure 3:
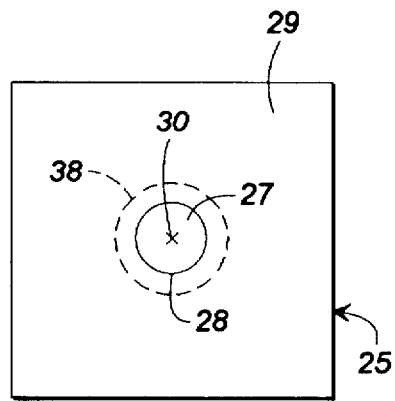
FIG. 3 is a plan view of the cover.
Figure 4:
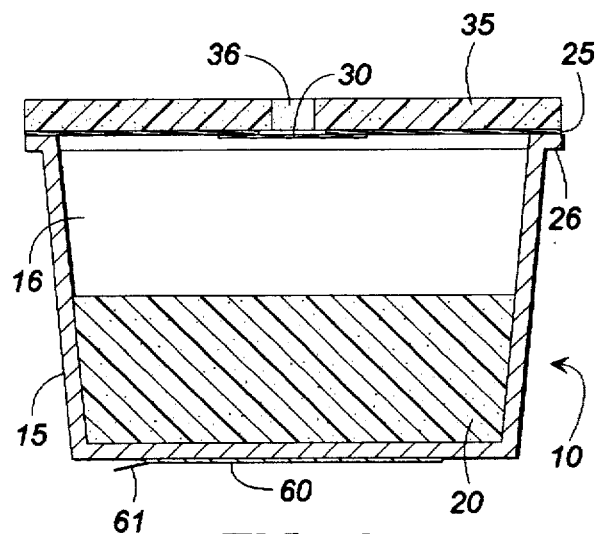
FIG. 4 is a side cross-sectional view of the preferred embodiment of the fluid collection device taken along line 4—4 of FIG. 1.

The closing layer 29 further comprises an aperture 28 in the center thereof that is covered and sealed by a layer of a synthetic elastic material 27. As is shown in FIG. 3, the layer of elastic material 27 is heat sealed to the closing layer 29 to form a leak resistant bond 38. Alternatively, the layer of elastic material 27 covers the entire open end 16 of container 15 and is heat sealed to the lip 26 surrounding the open end 16 of the container 15 and to the closing layer 29. While the elastic layer 27 is preferably between the container 15 and the closing layer 29, the order of the elastic layer 27 and the closing layer 29 may be reversed.

The layer of elastic material 27 can be any type of elastic or other material with sufficient elastic "memory," or shape retaining characteristics, to form a substantially leak resistant seal after the syringe 50 is inserted into the injection site 30 and removed. The layer of elastic material 27 preferably comprises a layer of die-cut thermoplastic rubber, such as that sold under the trademark Kraton™ by Shell Oil Company of Houston, Tex. Such a material comprises a mixture of approximately 65 percent styrene-ethylene/butylene-styrene block copolymer, 30 percent mineral oil, 15 percent polystyrene, and less than one percent each of an antioxidant/stabilizer, magnesium carbonate, and hydrated amorphous silica. The elastic layer 27 is preferably ten millimeters thick with a minimum tensile strength of 1000 pounds per square inch and elongation of a minimum of 450 percent.

Figure 5:
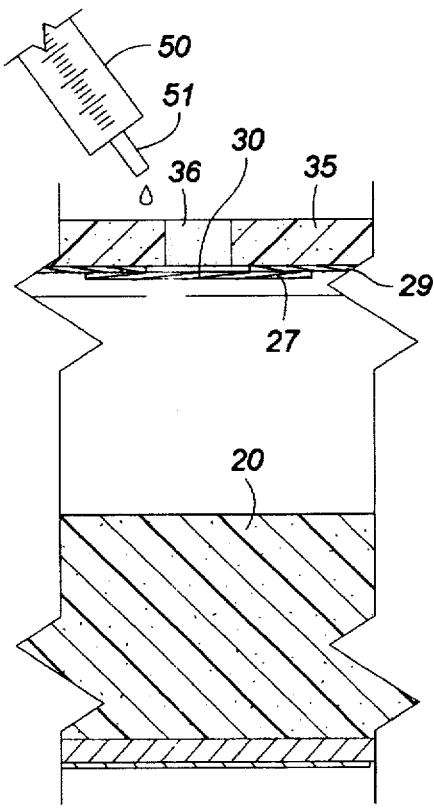
FIG. 5 is a partial side cross-sectional view of the injection port.
Figure 6:
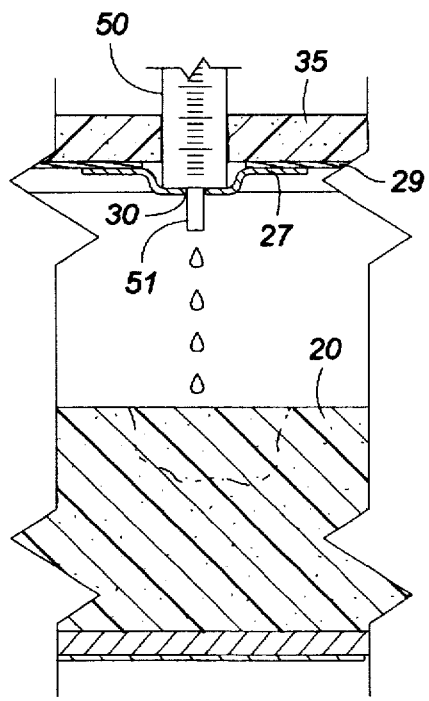
FIG. 6 is a partial side cross-sectional view of the injection port as penetrated by a syringe.

As is shown in FIGS. 5 and 6, the injection site or port 30 is a small die-cut hole in the layer of elastic material 27 positioned in the center thereof. The elastic material 27 stretches to allow the tip 51 of the syringe 50 to pass through and then returns to its original shape after the tip 51 is removed.

A second layer 35 of an absorbent material is then positioned on the cover 25. The second layer 35 can be any type of open cell foam or similar material. This second layer 35 does not need to be as absorbent as the layer of absorbent material 20 positioned within the container 15. In the preferred embodiment, a polyurethane foam with a density of about 1.2 pounds per cubic foot and a thickness of approximately 0.6 inch is used. The second layer 35 is cut to fit the cover 25 and is glued thereto. The second layer 35 has an aperture 36 therein to correspond to the injection site 30. The aperture 36 is generally labeled or marked by a "bulls-eye" 37 or similar marking so as to be clearly visible to the user.

Figure 7:
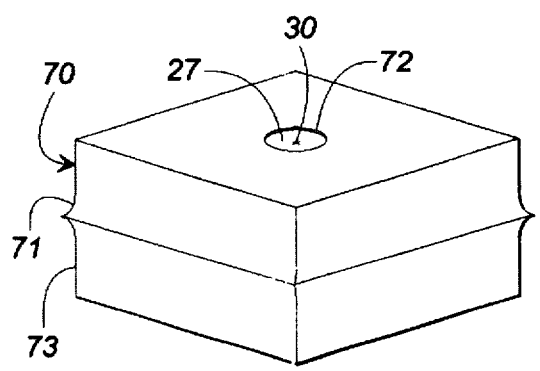
FIG. 7 is a perspective view showing an alternative embodiment of the fluid collection device.

As is shown in FIG. 7, an alternative embodiment of the present invention would include the use of a closed container 70 that simply contains an injection port 30 on one end. The container 70 has an upper casing 71 with an aperture 72 and a lower casing 73. In a manner similar to the previous embodiments, the layer of absorbent material 20 is positioned within lower casing 73 of the container 70 and the aperture 72 of the upper casing 71 is enclosed with the layer of elastic material 27 with the injection port 30. The two casings 71, 73 are sealed together by heat sealing, adhesives, or other bonding means. The upper casing 71 is then preferably covered with the second layer 35 of absorbent material.

Other alternatives for the container 15 will readily present themselves to those skilled in the art. The container 15 is preferably any shape that can be enclosed to be substantially leak resistant.

Similarly, while the preferred and other embodiments of the invention use a second layer 35 of an absorbent material on top of the cover 25 to absorb droplets of fluid that may splash on to the device 10, the substantially leak resistant nature of the device 10 is not compromised by the lack of such a layer.

Prior to use, the device 10 is sterilized in a vacuum chamber (not shown) by injecting gases such as ethylene oxide to bathe the device 10. The gas is then withdrawn and the device 10 is again bathed. Alternatively, the device 10 may be sterilized in any conventional manner. The device 10 is then placed and sealed in a sterile package (not shown) for distribution and storage.

In use, the device 10 is placed on the back table of an operating room, laboratory, or other sterile environment. The pull tab 61 on the adhesive layer 60 is removed and the device 10 is secured to the top of the table or other convenient position. A doctor, nurse, or other medical worker can then safely drain the contents of the syringe 50 or other medical instrument into the device 10.

As is shown in FIGS. 5 and 6, the tip 51 of the syringe 50 is inserted into the injection port 30 such that the tip 51 expands the elastic material 27 of the injunction port 30. The doctor, nurse, or other medical worker then empties the syringe 51 such that the fluid therein is absorbed into the layer of absorbent material 20. There is sufficient clearance for the tip 51 of the syringe 50 to empty its contents into the layer of absorbent material 20 without contacting the material 20. The layer of absorbent material 20 insures that there is no sloshing or splashing of the contaminated fluid. The syringe 50 is then removed from the device 10 and the elastic material 27 of the injection port 30 returns to its original size and shape to prevent the passage of fluids.

After the syringe 50 is removed and the injection port 30 returns to its original size, the device 10 is substantially spill and leak resistant. Because of the use of the layer of absorbent material 20 in conjunction with the leak resistant injection port 30, the device 10 is substantially resistant to spills or splashes even if dropped or tilted. While no device can completely eliminate the possibility of such spills and while it may be possible for some fluid to escape through the small injection port 30, any such fluid would be quickly absorbed by the second layer 35 of absorbent material to minimize the possibility of human contact.

In the event that the user misses the injection port 30 and punctures the cover 25, the leak resistant nature of the device 10 should not be compromised if the layer of elastic material 27 covers the entire open end 16 of the container 15. If, however, the elastic layer 27 does not extend over the puncture site, the integrity of the seal may be somewhat compromised though the second layer 35 of absorbent material should prevent or slow any leakage.

As is shown in FIG. 5, while the syringe 50 is being inserted into or removed from the device 10, any fluid that either seeps out or is accidentally forced out of the syringe 50 and on to the device 10 is absorbed by the second layer of absorbent material 35. The fluid is absorbed rather than splashing or spraying off of the cover 25 and possibly contacting the user. Any such fluid is quickly absorbed by the second layer of absorbent material 35 to prevent human contact.

After use, the device 10 can be quickly disposed of in any conventional fashion to ensure compliance with government regulations. The leak resistant and spill resistant nature of the device 10 lessens the possibility of contact by the user when transporting and disposing of the fluids contained therein.

The subject invention therefore results in a splash resistant and spill resistant back table collection system. The invention can easily dispose of fluids in a safe and sterile matter. The invention provides a disposable means to collect fluids while limiting the possibilities of contact by the user with the fluids due to splashing or spilling. The invention absorbs fluids injected therein and resists leaking. Further, the invention absorbs fluids that are splashed or spilled thereon rather than having the fluids splash onto the user. The invention achieves these goals in a lightweight, inexpensive device.

From the foregoing description of the preferred embodiment and the several alternatives, other alternative constructions of the present invention may suggest themselves to those skilled in the art. Therefore, the scope of the present invention is to be limited only by the claims below and equivalents thereof.

We claim:

1. A back table collection device for draining a syringe, comprising:
   a plastic container with an open end;
   at least one layer of an absorbent foam positioned within said plastic container;
   a layer of an elastic material sealing said open end of said plastic container;
   a hole positioned in the center of said layer of elastic material, said hole being substantially leak resistant in its relaxed state and stretching to substantially the size of the tip of said syringe in its expanded state; and
   a second layer of an absorbent material completely covering said layer of elastic material for substantially absorbing any droplets of fluid that may escape from said syringe.

2. The back table collection device of claim 1 wherein said layer of an absorbent material comprises large pore foam.

3. The back table collection device of claim 2 wherein said layer of large pore foam comprises reticulated ester filter foam.

4. The back table collection device of claim 1 wherein said second layer of an absorbent material comprises polyurethane open cell foam.

5. The back table collection device of claim 1 wherein said layer of an elastic material comprises thermoplastic rubber.

6. The back table collection device of claim 1 wherein said layer of an elastic material is heat sealed to said container.

7. The back table collection device of claim 1 further comprising a waterproof cover layer positioned between said elastic layer and said second layer of an absorbent material.

8. The back table collection device of claim 7 wherein said waterproof cover layer comprises high density polyethylene fibers.

9. The back table collection device of claim 1 wherein said container has sufficient clearance between said elastic layer and said layer of an absorbent material to permit the entry of said syringe tip into said hole without said syringe tip contacting said layer of absorbent material.

10. The back table collection device of claim 1 wherein said container has tapered sides to resist tipping.

11. The disposable back table collection device of claim 1 wherein said container further comprises a bottom end and wherein said bottom end has a layer of adhesive tape positioned thereon.

* * * * *